(12) United States Patent
Gilkerson et al.

(10) Patent No.: US 9,731,137 B2
(45) Date of Patent: Aug. 15, 2017

(54) SYSTEMS AND METHODS TO IDENTIFY THE INABILITY TO EXERCISE TO DESIRED CAPACITY

(71) Applicant: Cardiac Pacemakers, Inc., St. Paul, MN (US)

(72) Inventors: James O. Gilkerson, Stillwater, MN (US); Kenneth P. Hoyme, Plymouth, MN (US); James R. Kalgren, Lino Lakes, MN (US); David L. Perschbacher, Coon Rapids, MN (US); Les N. Peterson, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 420 days.

(21) Appl. No.: 13/932,135

(22) Filed: Jul. 1, 2013

(65) Prior Publication Data

US 2014/0012346 A1 Jan. 9, 2014

Related U.S. Application Data

(60) Provisional application No. 61/667,799, filed on Jul. 3, 2012.

(51) Int. Cl.
*A61N 1/365* (2006.01)
*A61N 1/372* (2006.01)
*A61N 1/37* (2006.01)

(52) U.S. Cl.
CPC ..... *A61N 1/36585* (2013.01); *A61N 1/36514* (2013.01); *A61N 1/37247* (2013.01); *A61N 1/3702* (2013.01); *A61N 1/37258* (2013.01); *A61N 1/37264* (2013.01); *A61N 1/37282* (2013.01)

(58) Field of Classification Search
CPC ............ A61N 1/36514; A61N 1/36542; A61N 1/36585; A61N 1/36592; A61N 1/37; A61N 1/3702; A61N 1/37241; A61N 1/37258

See application file for complete search history.

(56) References Cited

U.S. PATENT DOCUMENTS

| | | |
|---|---|---|
| 5,190,035 A | 3/1993 | Salo et al. |
| 6,190,324 B1 * | 2/2001 | Kieval et al. ................ 600/510 |
| 6,564,095 B1 | 5/2003 | Stahl et al. |
| 8,112,148 B2 | 2/2012 | Giftakis et al. |
| 9,357,935 B2 | 6/2016 | Gilkerson et al. |

(Continued)

OTHER PUBLICATIONS

Ruiter, Jacob H. et al., "The Feasibility of Fully Automated Pacemaker Advise in Treating Atrial Tachyarrhythmias", PACE, vol. 33 May 2010, 605-614.

(Continued)

*Primary Examiner* — Joseph Dietrich
(74) *Attorney, Agent, or Firm* — Pauly, DeVries Smith & Deffner, LLC

(57) ABSTRACT

The current technology is relevant to a system having a programming device capable of communication with an implantable medical device, where the programming device is configured to identify a patient condition comprising the patient's inability to exercise to a desired capacity, configured to notify a clinical user of the identified condition and configured to identify a therapy appropriate for the identified condition.

17 Claims, 13 Drawing Sheets

(56) References Cited

U.S. PATENT DOCUMENTS

| | | | |
|---|---|---|---|
| 2001/0037069 A1* | 11/2001 | Carlson | A61B 5/222 600/510 |
| 2007/0299317 A1 | 12/2007 | Hoyme et al. | |
| 2008/0157980 A1 | 7/2008 | Sachanandani et al. | |
| 2014/0213859 A1 | 7/2014 | Gilkerson et al. | |

OTHER PUBLICATIONS

"Non-Final Office Action," for U.S. Appl. No. 14/163,087, mailed Jul. 17, 2015 (12 pages).

"Restriction Requirement," for U.S. Appl. No. 14/163,087, mailed Apr. 20, 2015 (5 pages).

"Final Office Action," for U.S. Appl. No. 14/163,087 mailed Nov. 20, 2015 (10 pages).

\* cited by examiner

SYSTEMS AND METHODS TO IDENTIFY THE INABILITY TO EXERCISE TO DESIRED CAPACITY

This application is a non-provisional application claiming priority to U.S. Provisional Application No. 61/667,799, filed Jul. 3, 2012, the entire contents of which is incorporated herein by reference.

FIELD OF THE INVENTION

The current technology generally relates to programming of medical devices. More specifically, the current technology relates to systems and methods of identifying and communicating appropriate programming parameters in implantable medical devices (IMDs).

BACKGROUND

Implantable medical devices (IMDs) can be used to provide pacing therapy to patients who have cardiac rhythm problems. For example, an implanted cardiac rhythm management (CRM) device can be used to provide pacing therapy to a patient with sinus node dysfunction, where the heart fails to properly initiate depolarization waves, or an atrio-ventricular conduction disturbance, where the conduction of depolarization waves through the heart tissue is impaired.

At each follow-up appointment with a patient with an IMD such as a CRM, the clinician reviews information on multiple screens and reports, analyzes the information and determines which parameters are most appropriate for the IMD. Currently, some patient management systems can provide system recommendations of programming parameters based on patient-specific medical data including sensor data. Physicians would benefit from systems that identify specific patient indications and conditions and determine whether the IMD is programmed appropriately for the patient indications and conditions.

SUMMARY OF THE INVENTION

In one embodiment, a method includes identifying a patient condition, where the patient condition includes the patient's inability to exercise to a desired capacity using an implantable medical device. The method further includes notifying a clinical user of the identified condition. The method further includes identifying a therapy appropriate for the identified condition.

In another embodiment a system includes an implantable medical device configured to collect cardiac data from a patient and a programming device comprising a user interface and capable of communication with the implantable medical device to collect the cardiac data. The programming device is configured to program the implantable medical device, to identify a patient condition comprising the patient's inability to exercise to a desired capacity using the cardiac data, and notify a clinical user of the identified condition using the user interface.

BRIEF DESCRIPTION OF THE DRAWINGS

The invention may be more completely understood and appreciated in consideration of the following detailed description of various embodiments of the invention in connection with the accompanying drawings.

DETAILED DESCRIPTION

The technology disclosed herein relates generally to a medical device system for use with patients having an implantable medical device. The system identifies a patient condition to a clinical user of the system. The system uses information from the implantable medical device, such as cardiac data, to identify the patient condition. The system notifies the clinical user of the system of the identified patient condition. The system also identifies a therapy appropriate for the identified condition.

One example of a patient condition for a patient having a CRM device is the inability to exercise to the desired capacity. CRM devices are programmed to operate within a particular beat rate or heart rate (HR) range including a particular upper rate limit (URL) or maximum tracking rate (MTR). The MTR is the maximum heart rate at which the CRM will pace the heart. Often the MTR is selected conservatively and so is lower than a rate that the patient's heart would otherwise achieve. The clinician may have a minimum familiarity with the level of activity reached by the particular patient in the patient's varied activities. The actual proper HR range for the patient may well extend above that initially programmed. This being the case, the CRM device may repeatedly reach the URL or MTR because of naturally occurring sinus rhythms. If the CRM device does not provide the patient with a high enough HR during exercise or other active periods, the patient may experience lower than desirable cardiac output during exercise and discomfort during exercise.

As discussed above, at each follow-up appointment with a patient with an IMD such as a CRM, the clinician reviews information on multiple screens and reports, analyzes the information and determines which parameters are most appropriate for the IMD. The system described herein can identify patient conditions to the clinician, such as the inability to exercise to the desired capacity, at these follow up appointments, or at other times, and can also provide an appropriate therapy option. Some current systems are configured to recommend CRM programming parameters to a user, usually based on default settings, but the inventors are not aware of systems in use that identify patient conditions and notify the clinician of the patient condition. As used herein, a condition is a diagnosis or symptom.

While this technology can be applied to a variety of medical systems, including non-implantable devices, the implementation described herein will be with regard to implantable medical devices, particularly cardiac devices.

Medical Device Details

Figure 1:
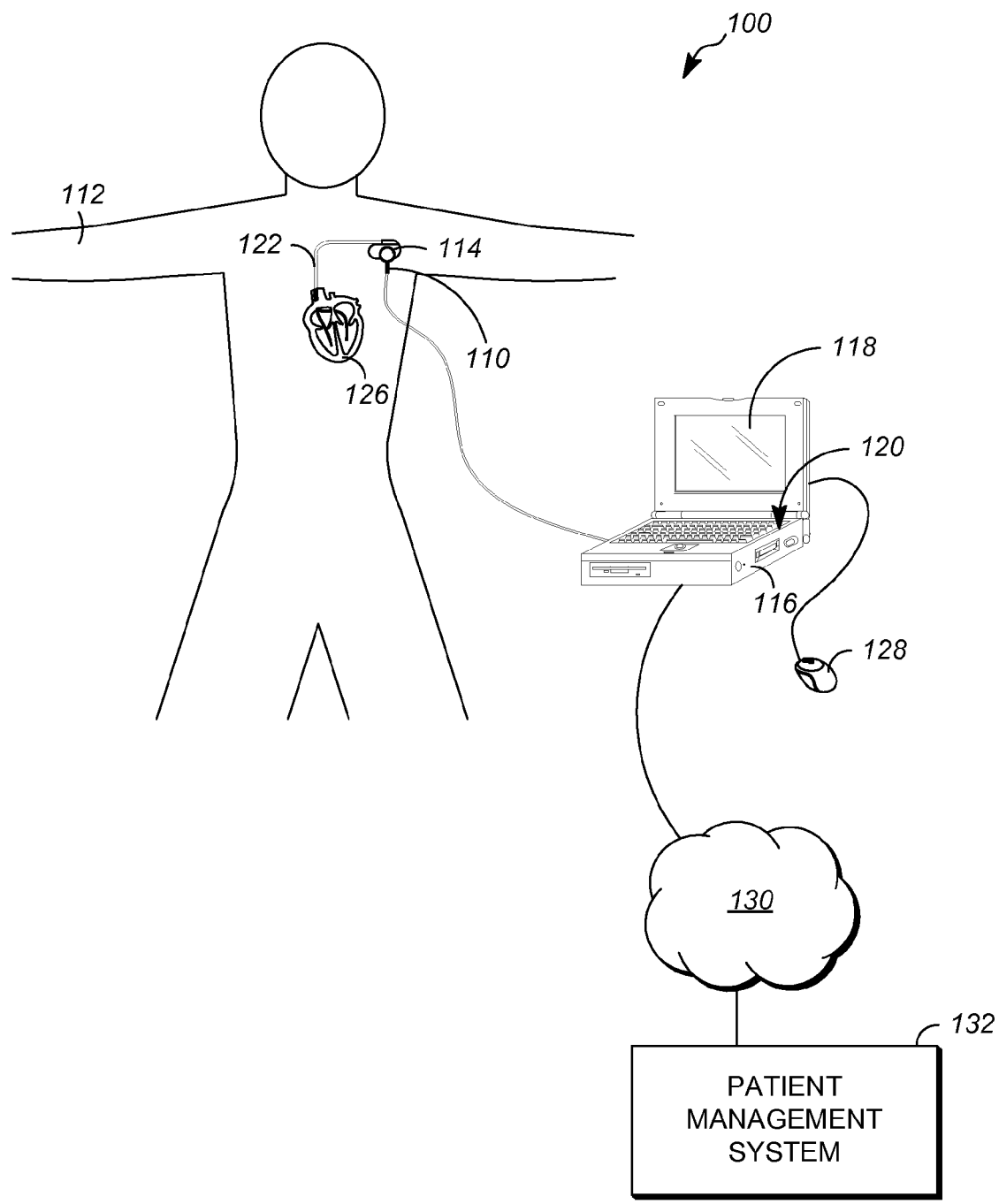
FIG. 1 is a schematic diagram of an exemplary implementation of a cardiac rhythm management (CRM) system, including an implanted CRM device, a programming device, and a patient management computer system, consistent with at least one embodiment of the technology disclosed herein.

FIG. 1 is a schematic of an exemplary cardiac rhythm management (CRM) system 100, consistent with at least one embodiment of the technology disclosed herein. The system 100 can include an implantable medical device 114 disposed within a patient 112. The implantable medical device 114 can include pacing functionality. The implantable medical device 114 can be of various types such as, for example, a pacemaker, a cardioverter-defibrillator, a cardiac resynchronization device, or the like. In some embodiments, the implantable medical device 114 can include one or more leads 122 disposed in or near the patient's heart 126. In some embodiments, the implantable medical device does not include leads. In one embodiment, the implantable medical device does not include leads and is configured to be implanted just below the patients skin and provide electrical impulses to stimulate the heart.

The implantable medical device 114 can include one or more implantable sensors in order to gather patient 112 data. For example, the implantable medical device 114 can include an activity level sensor which can be an accelerometer, a respiration sensor, a blood pressure sensor, and/or other sensors.

Programming Device Details

The implantable medical device 114 can be in communication with a programming device 116 or user interface. The programming device 116 is also in communication with the implantable sensor of the implantable medical device 114, and/or one or more other implantable sensors. In some embodiments, communication between the implantable medical device 114 and the programming device 116 can be via inductive communication through a wand 110 held on the outside of the patient 112 near the implantable medical device 114. However, in other embodiments, communication can be carried out via radiofrequency transmission, acoustically, or the like. The implantable medical device 114 can be configured to store data over a period of time and periodically communicate with the programming device 116 in order to transmit some or all of the stored data.

The programming device 116 can be for example, a programmer, a programmer/recorder/monitor device, a computer, an advanced patient management system, a personal digital assistant (PDA), or the like. A programming device is one example of a user interface. As used herein, the term programming device 116 refers to a device that programs implanted devices and records data from implanted devices. The programming device may also allow monitoring of the implanted device. Exemplary programmer/recorder/monitor devices include the Model 3120 Programmer, available from Boston Scientific Corporation, Natick, Mass. The programming device 116 can include a user interface such as a keyboard 120, a mouse 128, a touch screen, or more than one such device to receive user input. The programming device 116 can also include a video output channel and a user interface such as a video display 118 for displaying videos, user prompts, device operation parameters, settings, recommendations, and the like. In addition, the video display 118 can also be equipped with a touch screen, making it into a user input device as well.

The programming device 116 can display real-time data and/or stored data graphically, such as in charts or graphs, and textually through the user interface screen. The programming device 116 can display parameters associated with the medical device 114. Parameters associated with the medical device 114 can be device operational parameters, patient indications relevant to the medical device 114, and the like. In at least one embodiment, the parameters associated with the medical device 114 can include system-recommended parameters that are formulated by the system. In addition, the programming device 116 can prompt a user for particular data. In addition, the programming device 116 can also notify a clinical user of an identified patient condition, such as the patient's inability to exercise to the desired capacity. The notification can be in the form of an alert on the programming device screen 118, a sound, a text display, or a combination of these. The programming device 116 can also display options for a therapy appropriate for the identified condition. The programming device 116 can display one or more selectable options for a therapy appropriate for the identified condition and can receive input from the clinical user selecting one of the options.

The programming device can also display a rationale for the conclusion that a condition has been identified. Also, in response to an input to turn off or inappropriately modify the therapy appropriate for the condition, the programming device 116 can deliver an alert to a user communicating that the requested modification is inappropriate for the identified condition.

The programming device 116 can input and store a user's response to the various programming prompts. The programming device 116 can also display indications of system confidence levels relative to particular data or operation parameters based on a variety of factors including sensor reliability, age of a patient's electronic files, past accuracy of the data or operation parameters, and the like. The programming device can also display guidance to a user regarding data accuracy.

In various embodiments, the programming device 116 is in communication with a patient management system 132. The patient management system 132 can additionally be in communication with electronic patient medical records in a variety of embodiments. The communication link 130 between the programming device 116 and the patient management system 132 may be via phone lines, the Internet, or any other data connection. In another embodiment, the programming device 116 is not in direct communication with a patient management system 132, but can be in indirect communication with the patient management system 132. In another embodiment, the programming device is not in communication with a patient management system 132.

The programming device 116 is capable of changing the operational parameters of the medical device 114, and is therefore referred to as a programmer. Typically, programmers are used to interface with medical devices in a clinic or hospital setting. In this context, the user of the programming device 116 is a clinician, physician or trained technician.

Remote Programming Embodiment

Figure 2:
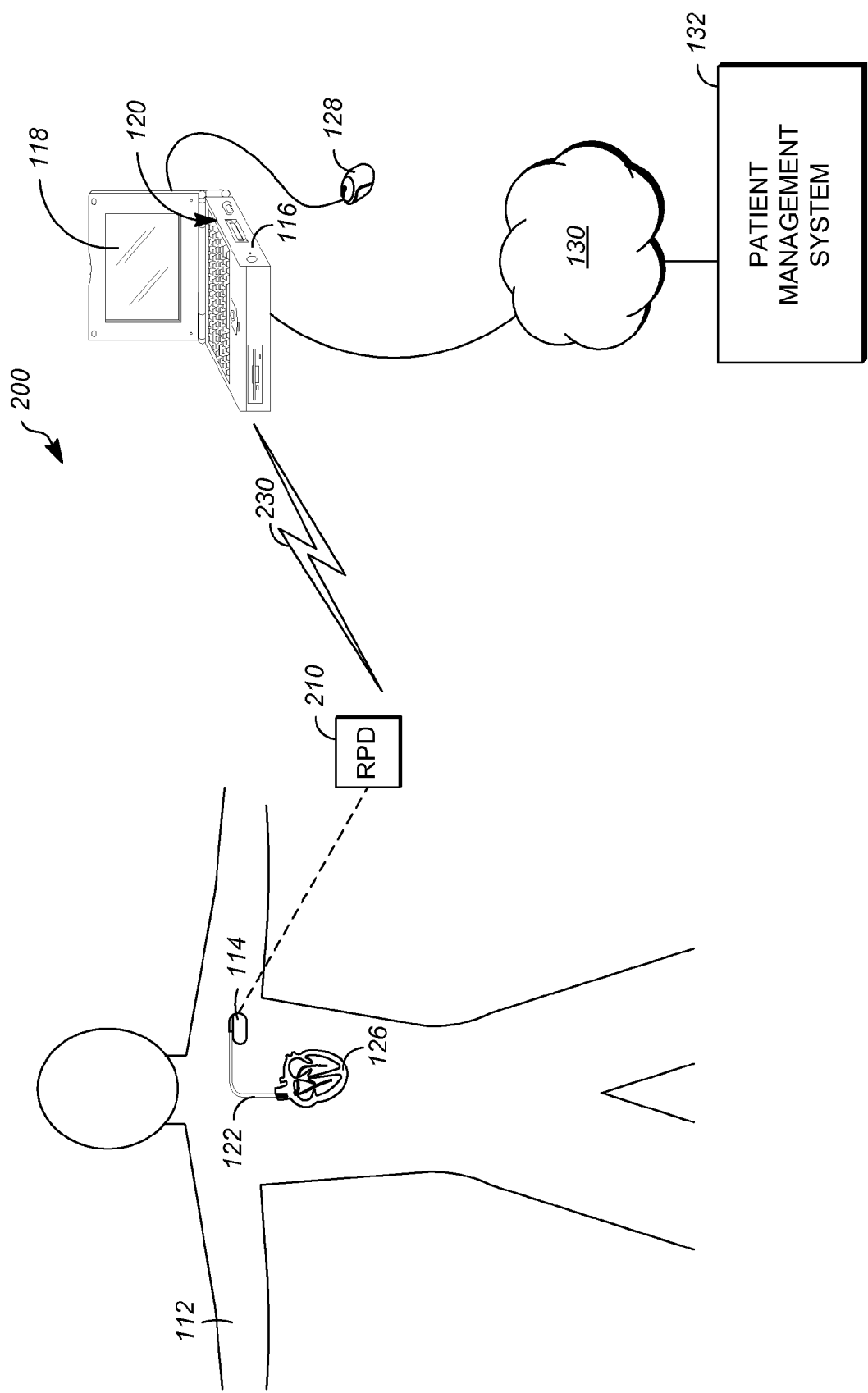
FIG. 2 is a schematic diagram of another exemplary implementation of a cardiac rhythm management (CRM) system, including an implanted CRM device, a remote programming device, a programming device, and a patient management computer system, consistent with at least one embodiment of the technology disclosed herein.

Now referring to FIG. 2, a CRM system 200 is illustrated which is designed for use when the programming device 116 and the patient 112 are in different locations, so that the programming device 116 is remote from the patient 112 and not physically present in the same space as the patient 112. For example, the patient 112 may be at his or her home while the clinician and the remote programming device is at a hospital which is a few miles away or hundreds of miles away. Like reference numbers between FIG. 1 and FIG. 2 indicate like elements. In the CRM system 200 of FIG. 2, a remote programming device 210 is in the patient 112 location and establishes communication with the implantable medical device 114. Communication between the remote programming device 210 and the implantable medical device 114 can be carried out by radiofrequency transmission, acoustically, or by inductive communication using a wand held on the outside of the patient 112 near the device 114.

The remote programming device 210 is in communication with a local programming device 116. The communication link 230 between the local programming device 116 and the remote programming device 210 may be via phone lines, the Internet, or any other data connection. Other details of the programming device 116 and the implantable medical device 114 are similar to as described with respect to FIG. 1.

Method Description

Figure 3:
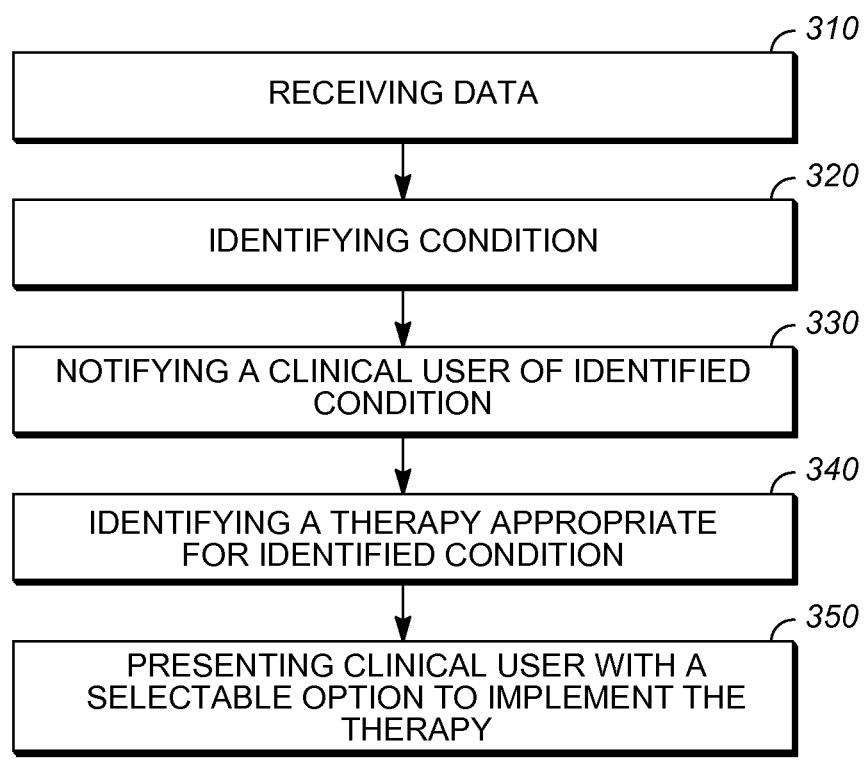
FIG. 3 is a flow chart depicting one method consistent with the technology disclosed herein.

FIG. 3 is a flow chart depicting one method consistent with the technology disclosed herein. The system receives data 310, identifies a condition of a patient 320 such as the patient's inability to exercise to a desired capacity, notifies or displays to a clinical user of the system of the identified condition 330, identifies to the clinical user a therapy appropriate for the identified condition 340, and presents the clinical user with a selectable option to implement the therapy 350.

Generally, the system can receive data 310 from a variety of sources. An implantable medical device and any implantable sensors can provide data including device operation parameters, patient indications, event counters, and any other data from the implantable medical device and/or from the implantable sensors. Examples of patient data available from a CRM device can include heart rate variability data, minute ventilation data, accelerometer data, a Wenckebach counter value and other data.

The implantable medical device can also provide data regarding the programming parameters that are in use at that moment in time and in the past, such as the maximum tracking rate and many other parameters.

The system can receive data from electronic medical records. The electronic medical records can include patient medical records, historical implantable medical device operation parameters, indications read or calculated from electronic charts and electronic medical records, user-entered indications, episodes, and trends in patient indications, as examples. The system can also receive data from a clinician. Such data can include patient symptom data or information, operation parameters, and the like.

The system can identify the inability to exercise to desired capacity in step 320 in a number of different ways.

Minute Ventilation or Accelerometer Sensor

One exemplary method is to use minute ventilation (MV) or accelerometer sensor data or both to determine a trend with which the patient's heart rate increases during exercise. In one embodiment, an MV sensor uses a transthoracic impedance measurement to monitor respiratory pattern changes and calculate a sensor-indicated heart rate. In one embodiment, an accelerometer sensor detects movement of the implanted device to monitor respiratory pattern changes, patient movement or both and uses that data to calculate a sensor-indicated heart rate. In one embodiment, the system uses information from both an MV sensor and an accelerometer to calculated a blended-sensor-indicated heart rate.

The system collects data during exercise and then compares the sensor-indicated heart rate to the actual heart rate that the patient is experiencing. In one embodiment, if the sensor-indicated heart rate is higher than the actual heart rate by at least a threshold amount, then the system concludes that the heart is not exercising to the desired capacity.

Heart Rate Variability Data

Another example of a technique to identify the inability to exercise to desired capacity is by analyzing heart rate variability data and determining from the heart rate variability data that the desired capacity for exercise requires a heart rate that is greater than at least one of a programmed maximum tracking rate, maximum sensor rate and maximum pacing rate in a CRM device. Single chamber CRM devices do not have maximum tracking rates but do have a maximum sensor rate and a maximum pacing rate. Dual chamber CRM devices may utilize both programmed maximum sensor and maximum tracking rates depending on the programming mode. If a device if programmed to VVIR, then the maximum sensor rate is applicable but the maximum tracking rate is not. If the device is programmed to DDD, then maximum tracking rate is applicable but maximum sensor rate is not. If the mode is DDDR, then both maximum tracking rate and maximum sensor rate are applicable.

Figure 4:
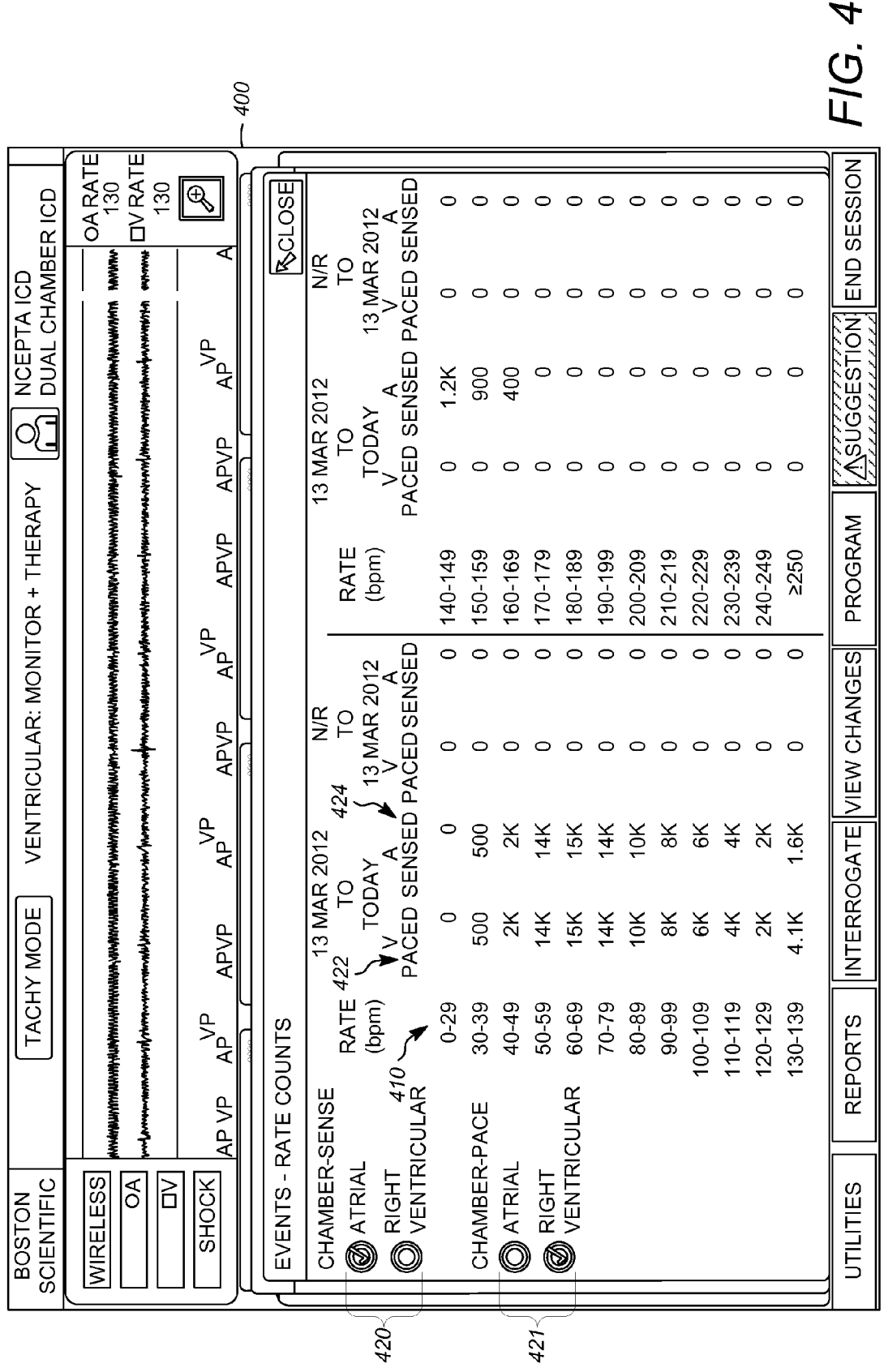
FIGS. 4-11 are example screenshots of a programming device consistent with the technology disclosed herein.

In dual chamber CRM devices, circuitry is provided for both sensing atrial and ventricular depolarization events and for pacing one or both of atrial and ventricular tissue. These CRM devices can keep a count of sensed atrial depolarizations. The counting module can be referred to as an A-sense counter. Each A-sense event can be recorded in a category according to what the patient's heart rate was at the time of the atrial contraction based on examining the atrial contractions. Also, the CRM device can track and categorize each ventricular pace event (V-pace), recording each V-pace in a category according to what the patient's heart rate was at the time of the V-pace based on examining the ventricular pacing. An example of a screen 400 displaying this type of rate count data or heart rate variability data is shown in FIG. 4. The rate categories are listed in the column 410 titled "Rate (bpm)" and in this example, indicates the heart rate within a 10 bpm range. Selection buttons 420 and 421 allow the user to select whether to view atrial rate counts or ventricular rate counts for pacing and sensing. On screen 400, atrial is selected for sensing and right ventricular is selected for pacing. As a result, the screen 400 displays sensed atrial rate counts and paced ventricular counts. The column 422 titled "V Paced" displays the count for ventricular pacing while the column 424 titled "A Sensed" shows the count for sensed atrial contractions.

In one embodiment, the identification algorithm compares the A-sense counts above the maximum tracking rate to the number of A-sense counts and V-pace counts that are close to the maximum tracking rate. For example, for a maximum tracking rate of 130 paces per minute (ppm), the method would identify the number of V-pace counts around the MTR and the number of A-sense counts around and above MTR (130 bpm).

The method would also gather information about the number of V-pace counts that are close to the upper limit of 130 ppm. In one example algorithm where MTR is programmed to 130 ppm, if the sum of V-sense and V-pace beats between 110 and 130 bpm is at least 20% greater than the sum of the A-sense and A-pace beats between 110 and 130 bpm, but less than 5% greater than the sum of the A-sense and A-pace beats between 110 and 140 bpm, then the system would suggest considering raising the MTR to 140 ppm.

In gathering the number of A-sense counts, no premature atrial contractions (PACs) should be counted in the total. If the number of A-sense counts above the MTR is similar to the number of A-sense counts near the MTR, then the maximum tracking rate will be recommended to be unchanged. If the number of A-sense counts above the MTR is significantly higher than the number of A-sense counts near the MTR, then the maximum tracking rate will be recommended to be increased. If the number of A-sense counts above the MTR is significantly lower than the number of A-sense counts near the MTR, then the maximum tracking rate will be recommended to be unchanged.

In a typical patient, heart rate variability usually increases, spikes and then consistently degrades as the heart rate increases. This is consistent with the example shown in FIG. 4. There may be A-Sense counts over 180 ppm but they should not be counted, similar to the rule for not counting PACs, since these may occur for reasons unrelated to exercise. In the example of FIG. 4, the maximum V-Pace is at the MTR of 130 ppm. The number of A-sense counts above 130 bpm (about 2500 counts) is higher than the number of A-sense counts near 130 bpm (about 1600 counts). The combined total of A-sense counts 2500 and 1600 are about the same as the V-pace total (4100) at MTR. As a result, the MTR could be raised a little higher to allow the patient to exercise at the desired capacity instead of being limited to the device MTR.

Wenckebach Counter Values

Another example of a technique to identify the inability to exercise to desired capacity is by comparing the Wenckebach counter value to a threshold value. If the Wenckebach counter value exceeds the threshold value, then a decision is made that the patient is unable to exercise to the desired capacity.

In a subject with normal sinus node activity and interrupted conduction system, the CRM device is able to sense an atrial depolarization (P-wave) and thereafter stimulate the ventricle in accordance with an established AV delay interval. This effectively mimics the heart's PR interval. The situation is complicated, however, by the possible occasional occurrence of an interfering retrograde conducted P-wave, possibly the result of a ventricular stimulating pulse, but one which is also sensed by the atrial sensing circuitry. Because the atrial sensing circuitry of the pacemaker cannot tell whether a sensed signal is a normal or retrograde conducted P-wave it will initiate another ventricular stimulation event. This may lead to pacemaker mediated tachycardia (PMT). To overcome this problem, dual chamber pacemakers are typically programmed to include a post-ventricular atrial refractory period (PVARP) during which atrial events are sensed but ignored. In this manner, if an atrial event occurs during PVARP due to retrograde conduction, an AV interval is not initiated and no ventricular stimulating pulse is generated as a result of the atrial event.

Wenckebach behavior is a type of undesirable upper rate limit behavior which negatively affects the patient. In Wenckebach behavior, as the atrial rate increases, the AV interval is lengthened so that the ventricular pacing interval does not exceed the MTR. As the atrial rate increases, a P-wave will eventually fall within PVARP and AV block will occur for that cardiac cycle. The successive lengthening of the AV interval leading to a missing cardiac cycle likewise causes short-term loss of AV synchrony and subsequent loss of cardiac output. The detection of Wenckebach behavior is important as an indication of a possible need for upper rate limit or maximum tracking rate (URL/MTR) adjustment. In one embodiment, if the Wenckebach counter value exceeds a threshold value, then a decision is made that the patient is unable to exercise to the desired capacity.

Cardiac Output

In another example of a method for identifying a patient's inability to exercise to the desired capacity, the CRM device determines the cardiac output and analyzes the result to see if it is too low. The cardiac output is the stroke volume multiplied by the heart rate. There are many different methods for using the CRM device to determine the cardiac output, such as the methods described in U.S. Pat. No. 5,190,035 to Salo et al. which use intrathoracic impedance. Other methods involve determining an aortic flow using Doppler shifting or by using perfusion sensors or other invasive and non-invasive techniques.

If cardiac output is too low according to the notification algorithm, the user is notified that the patient is unable to exercise to the desired capacity.

Notifying a Clinical User, Identifying a Therapy and Presenting a Therapy

Figure 5:
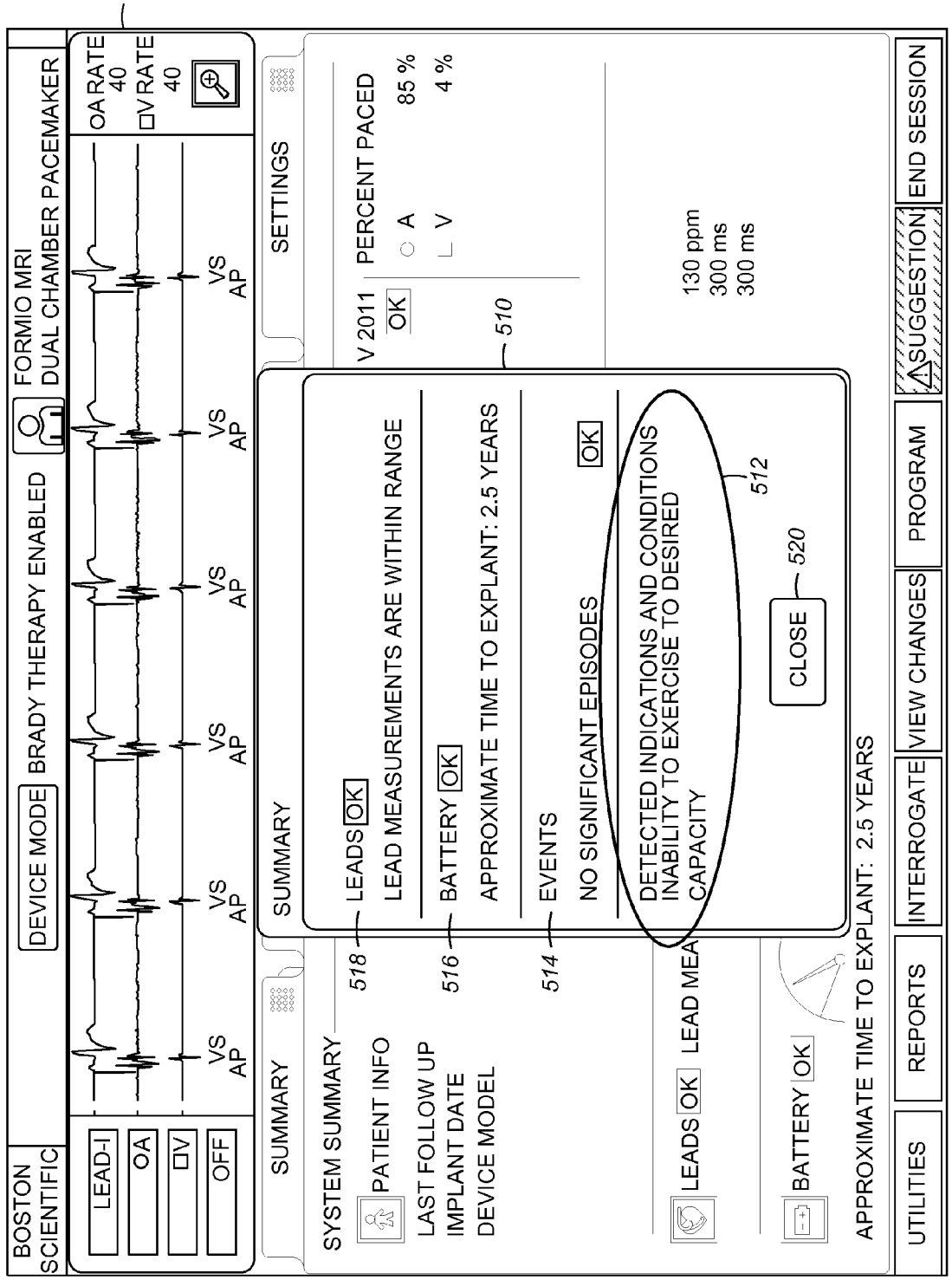

Again referring to FIG. 3, the system notifies the clinical user of the identified condition in step 320, identifies a therapy appropriate for the identified condition at step 340 and presents the clinical user with a selectable option to implement the therapy at step 350. FIGS. 5-11 show one example of a group of screen shots that can be used to accomplish these steps. Screen 500 of FIG. 5 shows an initial screen of a programming device. A summary dialog box 510 is presented to the user before providing access to the programming functions. The summary dialog box 510 includes a notification 512 of detected indications and conditions, and states "Inability to exercise to desired capacity" to indicate that this condition is present in the patient.

The summary dialog box 510 also includes an event notification 514. In the example of FIG. 5, the event notification 514 states that there have been no significant episodes. In other situations, the event notification "VF Therapy" may appear indicating that the patient has received therapy from the IMD for ventricular fibrillation. The event notification "VT Therapy" may appear indicating that the patient has received therapy from the IMD for ventricular tachycardia. The notification may indicate the zone in which the device detects therapy. The event notification "VT-1 Therapy" may appear indicating that the patient has received therapy for ventricular therapy in the VT-1 zone. The event notification "Atrial Episodes>48 hours" may appear indicating Atrial episodes lasting longer than 48 hours. The event notification "Non-Sustained Episodes" may appear indicating that episodes have occurred but that they were of a non-sustained nature.

The summary dialog box 510 also includes a battery notification 516. In one example, battery notification 516 states a timeframe until the end of the battery life or until device removal or explant is recommended. The summary dialog box 510 also includes a lead notification 518, such as a statement that all lead measurements are in range or a warning that a lead may be damaged. The summary dialog box 510 also includes a button 520 user input so that the user can acknowledge having viewed the notifications.

By clicking "Close" on the button 520, the user closes the summary dialog box 510 and views other programming device screens. For example, the user can next view screen 600 shown in FIG. 6, which displays the summary tab 610 of the programming device. The summary tab 610 includes a notification 620 of a detected patient indication or condition, in this example stating "Detected Inability to Exercise to Desired Capacity." A condition explanation button 630 is displayed as a part of the notification 620, and allows the user to get more information about the notification 620. A graphic is included on the condition explanation button 630, such as a magnifying glass, which indicates that further information can be obtained.

Figure 6:
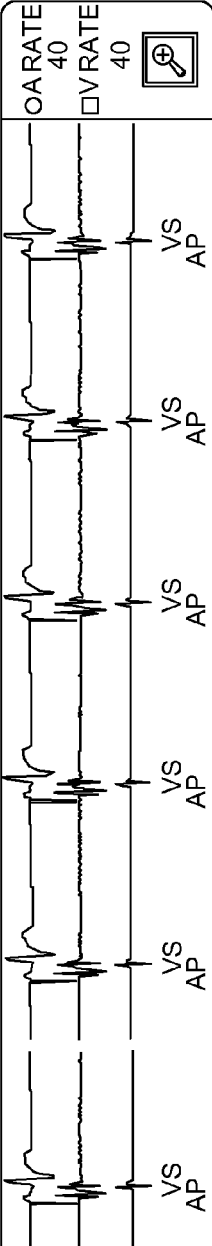

At the bottom edge of FIG. 6, many options for actions by the system or information from the system are presented to the user in the form of interactive buttons, including Utilities, Reports, Interrogate, View Changes, Program, Parameter/Alert Status (such as OK, Warning, Attention, Suggestion) and End Session. When the system has a suggestion for programming for the user that has not yet been adopted, the Suggestion button 635 is brought to the attention of the user with the use of a symbol and a special color, such as yellow, which is indicated in FIG. 6 with cross-hatching of the Suggestion button 635.

Figure 7:
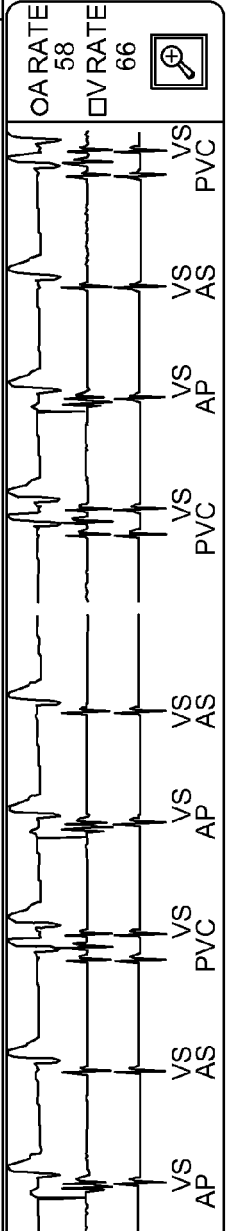

If the user selects the condition explanation button 630, the system displays screen 700 of FIG. 7 which provides a statement of the condition and provides a rationale for why the system concluded that the patient is unable to exercise to desired capacity in the screen portion 710. Screen 700 also includes an indications-based programming button 720 which the user can select to see selected indications and programming recommendations. Screen 700 also includes a checkbox 730 giving the user the option to improve the identified indication or condition, thereby providing the user with a selectable option to implement therapy appropriate to address the identified condition.

Figure 8:
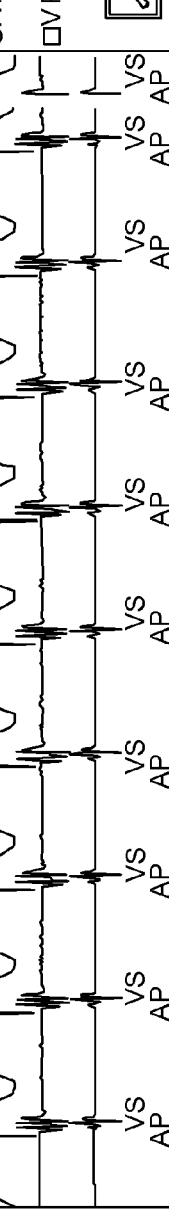

Screen 780 of FIG. 8 is one example of an indications-based programming display 782 where patient indications and conditions can be viewed, selected and unselected. A notification 784 of detected indications and conditions is displayed, and in this example includes "inability to exercise to desired capacity" along with a checkbox 786. The checkbox 786 is in a checked state to indicate that the system has detected this condition using an identification algorithm. The user can uncheck the checkbox 786 if the user has reached a different conclusion about the patient condition. The checkboxes and buttons described herein are all types of user input devices, and many different user input devices may be substituted for those described herein.

Screen 780 also includes a detected indications and conditions label and button 788 which allows a user to return to the more detailed information about of the patient's indications and conditions and the rationale for the detected indications and conditions of screen 700 of FIG. 7. Also, a view recommended settings label and button 790 provides a selectable option for the user to view the specific parameter settings that are recommended by the system to address the particular patient indications and conditions.

Figure 9:
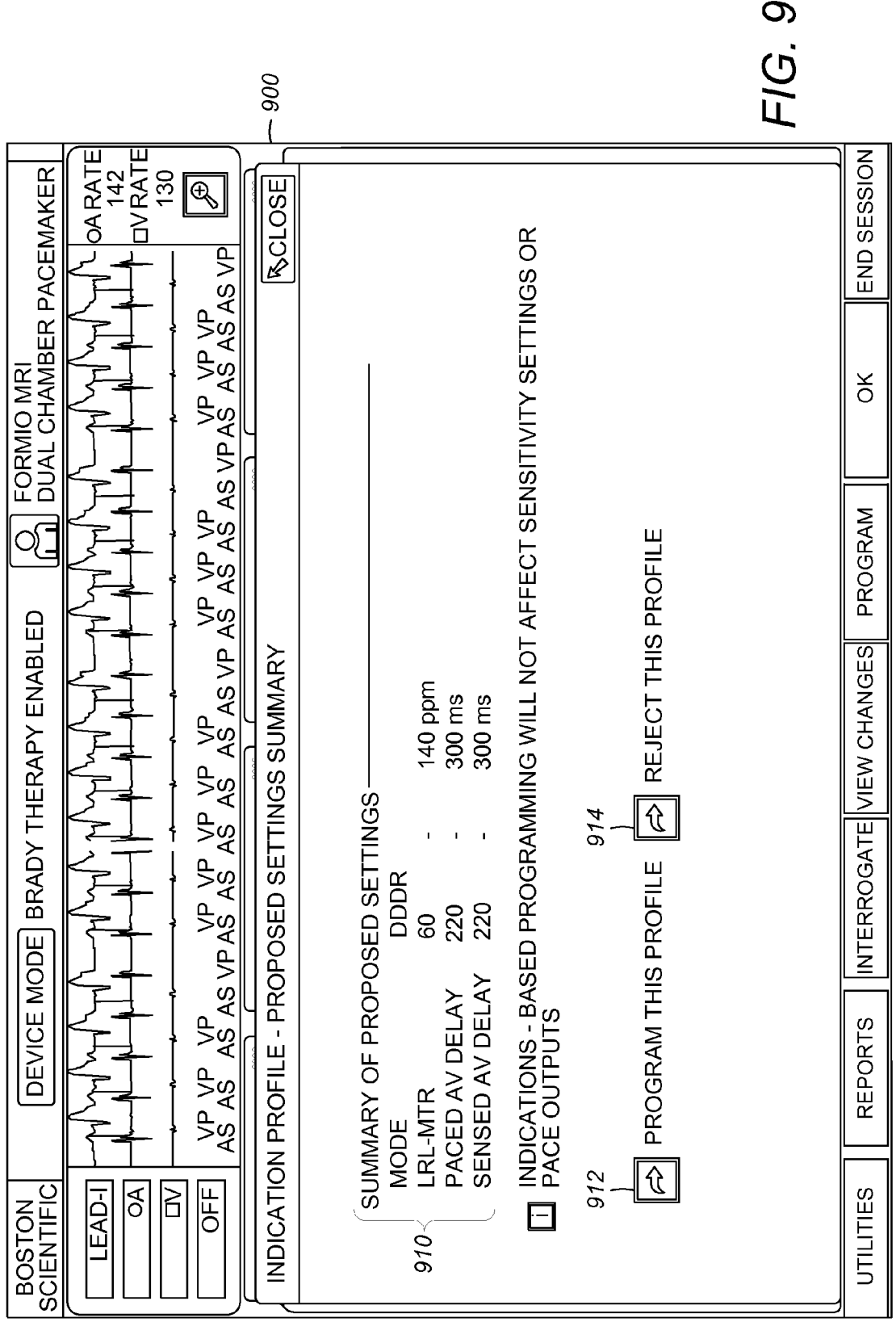

In one example, the system recommends an MTR value that is higher than the current MTR value be programmed for the CRM device to address the inability to exercise to the desired capacity. If the user selects the "View Recommended Settings" button 790 of FIG. 8, then screen 900 of FIG. 9 is displayed. In screen 900, a summary of proposed settings 910 is provided including setting the MTR to be 140 paces per minute instead of 130 paces per minute as it was previously programmed as shown at the Summary of Patient Information Screen 700. In screen 900, the user is also presented with a Program this Profile button 912 and a Reject this Profile button 914 to allow programming or rejecting the proposed settings to the implantable medical device.

Figure 10:
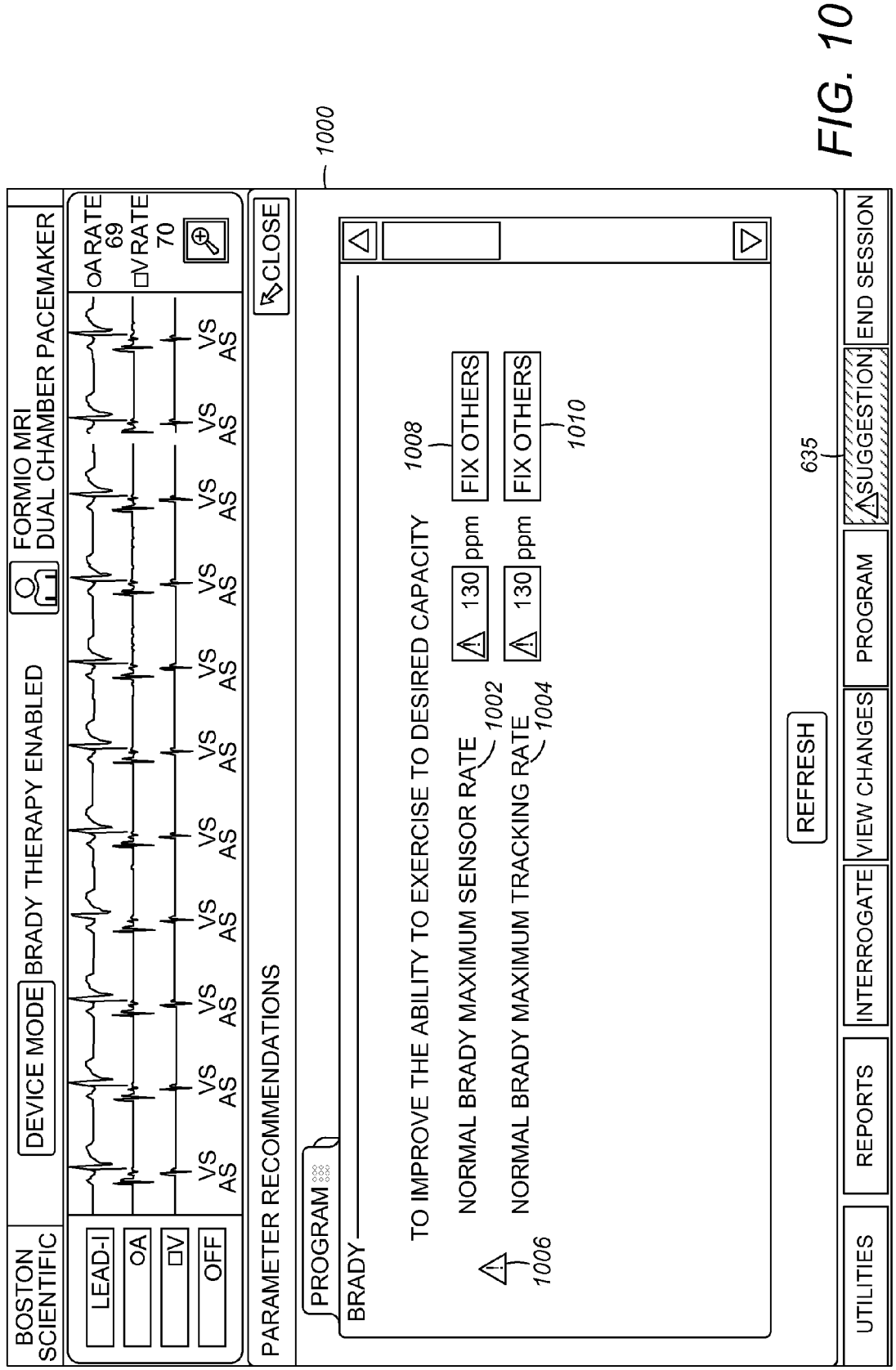

Other options also exist in the programming screens of FIGS. 5-12 to obtain more detailed information about the recommended setting changes. For example, by selecting the Suggestion button 635 of FIGS. 6-8, the user is brought to a summary of those parameters which can be modified to improve the identified condition. FIG. 10 provides an example of such a screen 1000, showing the Normal Brady Maximum Sensor Rate 1002 and the Normal Brady Maximum Tracking Rate 1004 at their programmed values of 130 ppm. Screen 1000 also shows a warning symbol 1006 indicating that the system has a different suggestion for these parameters.

Figure 11:
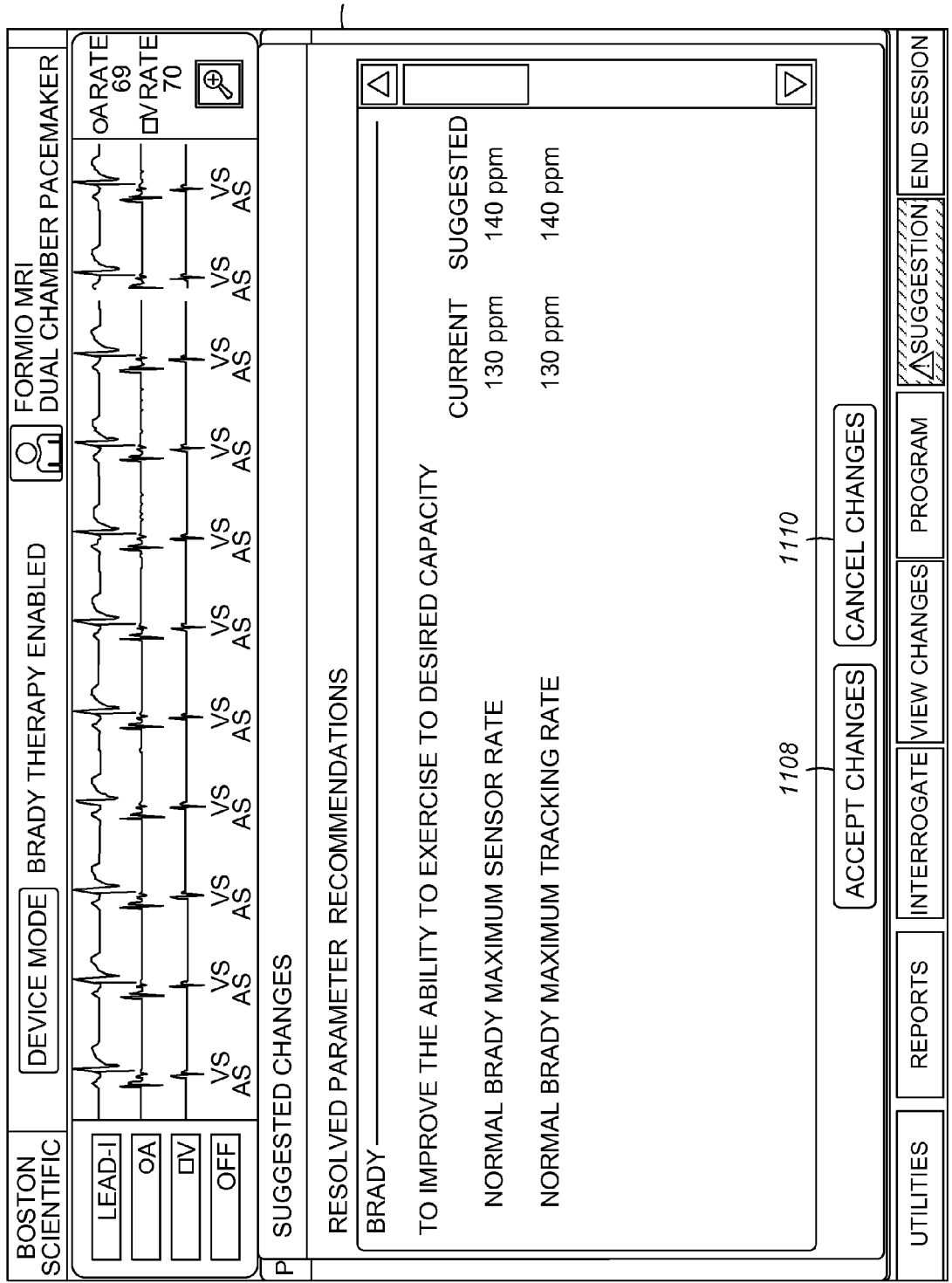

If the user selects either of the Fix Other buttons 1008, 1010 on the screen, the user is presented with screen 1100 of FIG. 11, providing Resolved Parameter Recommendations parameters. Screen 1100 of FIG. 11 shows that the current values for MSR and MTR are 130 ppm, but the suggested values are 140 ppm. The user has the option to accept the suggested parameter changes by selecting button 1108 or cancel the changes using button 1110.

In one example, in response to an input to turn off or inappropriately modify the therapy appropriate for the condition, the system delivers an alert to a user communicating that the existing therapy is appropriate for the identified condition. This alert can come in the form of the Suggestion button 635 being active and being presented to the user and brought to the user's attention with the color yellow, another color, a special symbol or more than one of these techniques. When the user presses the Suggestion button 635, the screen 1000 of FIG. 10 identifies to the user the parameters that are in conflict with the system's suggestions. When the user has accepted the suggested parameters, the Suggestion button 635 can become a dimmed OK button as shown in FIG. 9

FIGS. 5-11 show how the system communicates a treatment recommendation that conveys device operation parameters. Generally, the system makes a treatment recommendation based on data available to the system. The treatment recommendations will generally be consistent with recent patient indications and other data available to the system. The treatment recommendations can be communicated to a system user through a user interface, such as displayed on a screen. Other parameters associated with the medical device and the treatment recommendations can also be communicated to a system user. Each treatment recommendation can have a system confidence level associated therewith.

The system confidence level can be based on a variety of factors associated with the data, such as the reliability of a data source, historical patient data including event occurrences, past incorrectness of treatment recommendations, conflicting data, and so on. In a variety of embodiments the system provides an indication of the system confidence level of the treatment recommendations to the user, which can be expressed in a variety of ways including a percentage or number value, color code, text and so on. The treatment recommendations can be displayed for the caretaker on a user interface, who may decide to select or override one or more parameters.

The system can receive the clinical user's therapy selection through a variety of user interface devices such as a keyboard, touch screen, mouse, microphone, combinations thereof, and so on.

If the clinical user's therapy selection conflicts with system data, the system can display a notice to provide information to the user. The notice can be a warning indicating that the chosen treatment is not consistent with patient indications. The warning can also notify the system user of data that is in conflict with the therapy selection, or provide another explanation of the inconsistency. The system can also provide the user with rationale associated with the recommended parameter.

Programmer Hardware

Figure 12:
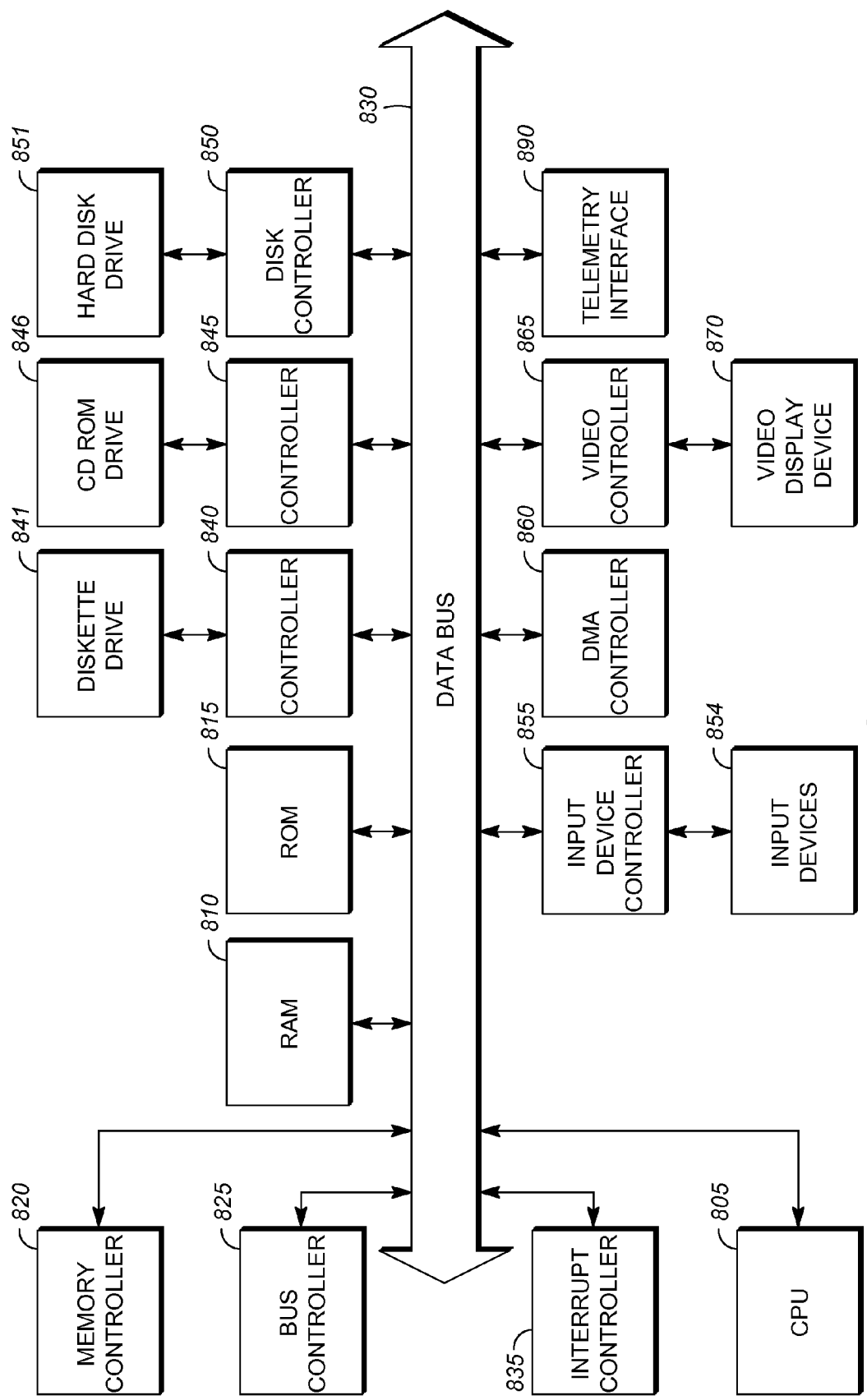
FIG. 12 is a schematic diagram of an implementation of the components of a programming device or user interface, in accordance with various embodiments.

Programming devices can include components common to many computing devices. Referring now to FIG. 12, a diagram of various components is shown in accordance with some embodiments of the invention. However, it is not required that a programming device have all of the components illustrated in FIG. 12.

In one embodiment, the programming device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of input devices 834. For example, a keyboard, touch screen, mouse, or more than one of these, can connected to bus 830 by input device controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 12.

Implantable Device Hardware

Figure 13:
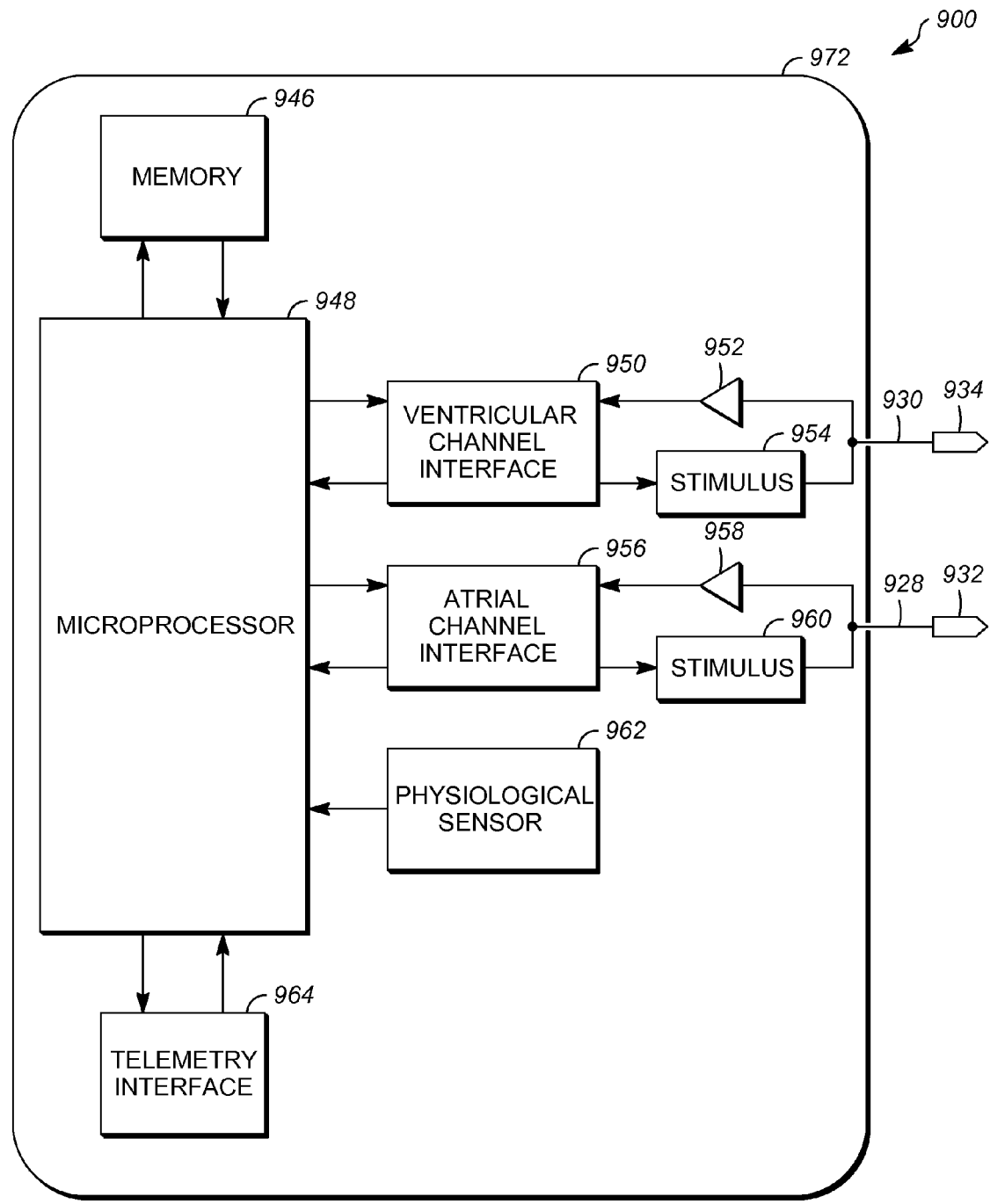
FIG. 13 is a schematic view of components of an implantable medical system in accordance with an embodiment of the invention.

Referring now to FIG. 13, some components of an exemplary implantable system 900, such as an implantable CRM device, are schematically illustrated. The implantable medical system 900 can include an implantable medical device 972 coupled to one or more stimulation leads 930 and 928. The implantable device 972 can also include other sensors such as an activity sensor 962.

The implantable device can include a microprocessor 948 (or processor) that communicates with a memory 946 via a bidirectional data bus. The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bidirectionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bidirectionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

We claim:

1. A method comprising:
   collecting cardiac data from a patient with an implantable medical device, the cardiac data comprising heart rate variability data;
   communicating, by a programming device, with the implantable medical device to collect the cardiac data, wherein the programming device is configured to program the implantable medical device;
   identifying, by the programming device, a patient condition comprising the patient's inability to exercise to a desired capacity using the cardiac data;
   notifying a clinical user of the identified condition with a user interface of the programming device; and
   identifying a therapy appropriate for the identified condition,
   wherein identifying the inability to exercise comprises analyzing the heart rate variability data and determining from the heart rate variability data that the desired capacity for exercise requires a heart rate that is greater than at least one of a programmed maximum tracking rate, a programmed maximum sensor rate and a programmed maximum pacing rate in a cardiac rhythm management device.

2. The method of claim 1 further comprising presenting the clinical user with a selectable option to implement the therapy appropriate for the identified patient condition.

3. The method of claim 1, further comprising, in response to an input to enable, disable or modify the therapy appropriate for the condition, delivering an alert to a user communicating that the requested modification is inappropriate for the identified condition.

4. The method of claim 1, wherein identifying the condition further comprises detecting a cardiac condition using a cardiac rhythm management device.

5. The method of claim 1, wherein notifying a clinical user of the identified condition comprises presenting an alert on a programmer.

6. The method of claim 1, wherein identifying the inability to exercise to the desired capacity further comprises comparing one or both of a minute ventilation rate and an accelerometer rate obtained through a diagnostic trend to an actual heart rate.

7. The method of claim 1, wherein identifying the inability to exercise to the desired capacity further comprises analysis of the Wenckebach counter value.

8. The method of claim 1 further comprising receiving data comprising at least one of patient symptom data, electronic medical record data and current programming parameters for the implantable medical device.

9. The method of claim 1 wherein notifying the clinical user of the identified condition further comprises displaying a rationale for the conclusion underlying the identified condition.

10. A system comprising:
an implantable medical device configured to collect cardiac data from a patient, the cardiac data comprising heart rate variability data;
a programming device comprising a user interface and capable of communication with the implantable medical device to collect the cardiac data, wherein the programming device is configured to program the implantable medical device, to identify a patient condition comprising the patient's inability to exercise to a desired capacity using the cardiac data, and notify a clinical user of the identified condition using the user interface,
wherein the programming device is configured to analyze the heart rate variability data and determine from the heart rate variability data that the desired capacity for exercise requires a heart rate that is greater than at least one of a programmed maximum tracking rate, a programmed maximum sensor rate and a programmed maximum pacing rate in a cardiac rhythm management device in order to identify the inability to exercise.

11. The system of claim 10 wherein the programming device is further configured to identify a therapy appropriate for the identified condition.

12. The system of claim 10 wherein the programming device is further comprising to present the clinical user with a selectable option to implement the therapy appropriate for the identified condition on the user interface.

13. The system of claim 10, the programming device further configured to, in response to an input to turn off or modify the therapy appropriate for the condition, deliver an alert to a user communicating that the requested change in therapy is inappropriate for the identified condition.

14. The system of claim 10, wherein the programming device is further configured to compare one or both of a minute ventilation rate and an accelerometer rate obtained through a diagnostic trend to an actual heart rate in order to identify the inability to exercise.

15. The system of claim 10, wherein the programming device is further configured to analyze a Wenckebach counter value in order to identify the inability to exercise.

16. The system of claim 10 wherein the programming device is configured to receive data comprising at least one of patient symptom data, electronic medical record data and current programming parameters for the implantable medical device.

17. The system of claim 10 wherein the programming device is configured display a rationale for the conclusion underlying the identified condition.

* * * * *